US006441170B1

(12) United States Patent
Mais et al.

(10) Patent No.: US 6,441,170 B1
(45) Date of Patent: Aug. 27, 2002

(54) METHOD OF PRODUCING 4,6-DICHLOROPYRIMIDINE WITH ACID CHLORIDES

(75) Inventors: Franz-Josef Mais, Düsseldorf; Günther Cramm, Leverkusen; Alexander Klausener, Pulheim; Guido Steffan, Odenthal, all of (DE)

(73) Assignee: Bayer Akitnegesellschaft, Leverkusen (DE)

( * ) Notice: Subject to any disclaimer, the term of this patent is extended or adjusted under 35 U.S.C. 154(b) by 0 days.

(21) Appl. No.: 10/019,092

(22) PCT Filed: Jun. 13, 2000

(86) PCT No.: PCT/EP00/05400

§ 371 (c)(1), (2), (4) Date: Dec. 19, 2001

(87) PCT Pub. No.: WO01/00592

PCT Pub. Date: Jan. 4, 2001

(30) Foreign Application Priority Data

Jun. 26, 1999 (DE) .......................................... 199 29 350

(51) Int. Cl.$^7$ ............................................ C07D 239/30
(52) U.S. Cl. ...................................................... 544/334
(58) Field of Search ......................................... 544/334

(56) References Cited

U.S. PATENT DOCUMENTS 5,677,453 A    10/1997  Cramm et al. ............... 544/334
5,719,285 A    2/1998   Steffan ....................... 544/334

FOREIGN PATENT DOCUMENTS

| EP | 745 593  | 12/1996 |
| EP | 761 653  | 3/1997  |
| GB | 2325224  | 11/1998 |
| WO | 95/29166 | 11/1995 |
| WO | 96/23776 | 8/1996  |

OTHER PUBLICATIONS

"Chlorination of Pyrimidines", Research Disclosure, GB, Industrial Opportunities LTD. Havant, No. 391, Nov. 1, 1996, pp. 690–691, XP00068093.

Shiao Min–Jen: "A convenient synthesis of Halogenated 2–chloropyridines by transformation of Halogenated 2–methoxypyridines under Vilsmeier–Haack conditions", Synthetic Communications., vol. 20, No. 19, 1990, pp. 2971–2977, XP000960608, Marcel Dekker, Inc., Basel., CH.

*Primary Examiner*—John M. Ford
(74) *Attorney, Agent, or Firm*—Joseph C. Gil; Richard E. L. Henderson

(57) ABSTRACT

The present invention relates to a process for preparing 4,6-dichloro-pyrimidine by reaction of 4-chloro-6-methoxypyrimidine with an acid chloride in the presence of a hydrogen halide.

6 Claims, No Drawings

METHOD OF PRODUCING 4,6-DICHLOROPYRIMIDINE WITH ACID CHLORIDES

The present invention relates to a process for preparing 4,6-dichloropyrimidine from 4-chloro-6-methoxypyrimidine. 4,6-Dichloropyrimidine is a valuable intermediate for preparing crop protection agents.

A number of processes for preparing 4,6-dichloropyrimidine are known, see, for example, WO 96/23776, EP-A-697 406, EP-A-745 593, WO 95/29166, DE-A19 53 129 and GB 2 325 224. However, these processes always start from 4,6-dihydroxypyrimidine.

It is also known (see Res. Discl. n 391, 690–691 (1996)) that 4,6-dichloropyrimidine can be reacted by reacting 4-chloro-6-methoxypyrimidine with a chlorinating agent of the formula $R_3PCl_2$. The chlorinating agent can be employed as such or be prepared in situ from a compound of the formula $R_3P=O$ and phosgene. It is additionally described therein that 4-chloro-6-methoxypyrimidine does not react with phosphorus oxychloride. The disadvantage of this process is that, as a rule, only a very incomplete reaction can be achieved and thus 4,6-dichloropyrimidine is obtainable only in low yields and low degrees of purity.

A process for preparing 4,6-dichloropyrimidine which is characterized in that 4-chloro-6-methoxypyrimidine is reacted with an acid chloride in the presence of a hydrogen halide has now been found.

Suitable acid chlorides are organic and inorganic acid chlorides, for example $PCl_3$, $POCl_3$, $PCl_5$, R—$PCl_2$, R—$PCl_4$, R—$POCl_2$ and $R_3PCl_2$, where R represents optionally substituted $C_6$–$C_{10}$-aryl or optionally substituted $C_1$–$C_{10}$-alkyl, acid chlorides of the formula R'—CO—Cl with R'= chlorine, $C_1$–$C_{10}$-alkoxy, $C_6$–$C_{10}$-aryloxy, —$OCCl_3$, —CO—Cl, $C_5$–$C_{11}$–heteroaryloxy with 1 to 3 heteroatoms from the group of N, O and S, whereas the alkoxy, aryloxy and hetaryloxy radicals may optionally be substituted, and $SOCl_2$.

It is furthermore possible to generate the required acid chloride in situ. For example, $R_3PCl_2$ can be generated from $R_3P$ and chlorine or from $R_3P=O$ and a chlorinating agent, for example $PCl_3$, phosgene or $SOCl_2$.

Suitable examples of hydrogen halides are: hydrogen chloride, hydrogen bromide and hydrogen iodide. Hydrogen chloride is preferred. The use of mixtures of hydrogen halides is also possible.

Hydrogen chloride can, for example, be employed as such in the form of a gas or be generated in situ from an excess of added acid chloride and a protic compound. A wide variety of protic compounds which cause no unwanted side reactions in the reaction mixture are suitable. Examples which may be mentioned are: water, alcohols and organic and inorganic acids.

It is preferred to add gaseous hydrogen chloride or generate it in situ. Gaseous hydrogen chloride is particularly preferably employed.

It is preferred to employ in the process of the invention at least 1 mol of acid chloride per mole of 4-chloro-6-methoxypyrimidine. It is preferable to employ 1.1 to 20 mol, particularly preferably 1.5 to 10 mol, of acid chloride per mole of 4-chloro-6-methoxypyrimidine. If the acid chloride is also employed as solvent or as starting material for the in situ generation of hydrogen halide, the preferred minimum amount of acid chloride is, of course, correspondingly higher.

In addition, at least 1 mol of hydrogen halide is employed per mole of 4-chloro-6-methoxypyrimidine. However, an excess of hydrogen halide is advisable to achieve a high conversion.

It is preferable to employ 1.1 to 25 mol of hydrogen halide, particularly preferably 2 to 10 mol of hydrogen halide, per mole of 4-chloro-6-methoxypyrimidine.

If it is wished to generate the abovementioned amounts of hydrogen halide in situ from a protic compound and an acid chloride, the protic compound is employed in amounts such that it generates the abovementioned amounts of hydrogen halide, that is to say, for example, to generate 1 mol of hydrogen chloride for example 0.5 mol of water or 1.0 mol of methanol is employed. In this case, it is also preferred to employ additional amounts of acid chlorides which are equivalent to the amounts of hydrogen chloride to be generated, for example to generate 1 mol of hydrogen chloride additionally 0.33 mol of phosphorus oxychloride or additionally 0.5 mol of thionyl chloride.

If an acid chloride which is liquid under the reaction conditions is used, it is possible to dispense with the addition of a solvent. Suitable solvents in principle are those which do not adversely affect the reaction to be carried out. Examples of solvents are aliphatic solvents such as alkanes, cycloalkanes and halogenoalkanes, aromatic solvents such as benzene, toluene, xylenes, chlorobenzene, chlorotoluenes, dichlorobenzenes, benzotrifluoride and p-chlorobenzotrifluoride, it being possible for the aliphatic and aromatic solvents optionally to be substituted further, nitrites such as acetonitrile and benzonitrile, N-containing solvents such as dimethylformamide, dimethylacetamide, N-methylpyrrolidone and cyclic ureas and ethers and polyethers of a wide variety of types.

The process of the invention can be carried out, for example, at temperatures in the range 0 to 200° C., preferably at 20 to 175° C., particularly preferably at 30 to 150° C. The pressure is not critical. It can be, for example, 0.1 to 50 bar, preferably 0.5 to 5 bar. Atmospheric pressure is particularly preferred.

It is possible to employ catalysts known in principle from the area of chemical reactions with acid chlorides, for example amides such as dimethylformamide, amines such as pyridine, morpholine or 1,8-diazobicyclo[5.4.0]undec-7-ene (=DBU) or phosphorus compounds such as triphenylphosphine or triphenylphosphine oxide.

Catalysts of these types can be employed, for example, in amounts of from 0.1 to 10 mol %, based on the 4-chloro-6-methoxypyrimidine. Preference is given to no additions of catalyst.

The process of the invention can be carried out in a wide variety of embodiments, for example batchwise, semicontinuously, continuously or semibatchwise (concerning the latter, see DE-A 195 31 299).

For example, acid chloride and, where appropriate, solvent can be added to solid or molten 4-chloro-6-methoxypyrimidine and, at the desired reaction temperature, either hydrogen halide can be passed in or a protic compound can be metered in. After the reaction is complete, the reaction mixture can be worked up in a manner known per se, for example a) by adding water to the reaction mixture and removing the 4,6-dichloropyrimidine, b) by distilling the complete reaction mixture, c) by first rechlorinating the used acid chloride with, for example, $PCl_3/Cl_2$ or $PCl_5$ and subsequently distilling and d) by directly extracting the 4,6-dichloropyrimidine from the reaction mixture with a suitable solvent and subsequently distilling the extract.

It is possible to choose for the rechlorination according to c) a semibatchwise procedure. The procedure for this can, for example, be such that 4-chloro-6-methoxypyrimidine and, for example, phosphorus oxychloride are heated to the reaction temperature, gaseous hydrogen chloride is passed in and, after partial conversion, for example 25 to 60 mol %, the appropriate amount of $PCl_3$ or a slight excess (for example of 5 to 10 mol %) is added, and the appropriate amount of chlorine is passed in. The passing in of hydrogen chloride is then continued, possibly interrupted once more and again rechlorinated with $PCl_3$ and chlorine in the amount corresponding to the conversion or a slight excess. With such a procedure for the process of the invention, the reaction mixture contains 4,6-dichloropyrimidine and only small residues (generally less than 2 mol %) of 4-chloro-6-methoxypyrimidine, phosphorus oxychloride, $PCl_3$ and hydrogen chloride after the end of the conversion and final rechlorination with $PCl_3/Cl_2$. This mixture can be worked up simply by distillation. It is possible with this procedure, for example, to add all the $PCl_3$ at the start of the passing-in of hydrogen chloride or in the first rechlorination.

The process of the invention represents a fundamentally novel method for preparing 4,6-dichloropyrimidine. In contrast to the disclosed literature, even simple acid chlorides such as phosphorus oxychloride react with 4-chloro-6-methoxypyrimidine directly to give 4,6-dichloropyrimidine if hydrogen halides are present.

The process of the invention can be carried out industrially without difficulty. Simply by passing in a hydrogen halide, in the simplest case hydrogen chloride, or metering in a protic compound, in the simplest case water, it is possible to react acid chlorides, in the simplest case phosphorus oxychloride, with 4-chloro-6-methoxypyrimidine to form 4,6-dichloropyrimidine. It is possible on use of liquid acid chlorides to do without solvents, which makes the subsequent workup extremely simple. The process of the invention additionally represents a considerable advance compared with the prior art described in Res. Discl. loc. cit. The two examples mentioned therein show that only incomplete conversion of 4-chloro-6-methoxypyrimidine to 4,6-dichloropyrimidine has taken place therein. This is particularly disadvantageous because 4,6-dichloropyrimidine and 4-chloro-6-methoxypyrimidine can be separated only very poorly by distillation. Under the conditions according to the invention, especially in the presence of hydrogen halide, the conversion takes place considerably faster and completely or nearly completely.

EXAMPLES

Example 1

90 parts by weight of phosphorus oxychloride and 10 parts by weight of 4-chloro-6-methoxypyrimidine were introduced into a stirred vessel. The mixture was heated with stirring to 100° C. and, at this temperature, 6 parts by weight of water were metered in at a constant rate over the course of 4 hours. The mixture was then stirred at 100° C. for 1 hour. After cooling to room temperature, 99.6 parts by weight of a reaction mixture whose HPLC analysis showed contents of 0.2% 4-chloro-6-methoxypyrimidine and 9.3 parts by weight of 4,6-dichloropyrimidine were obtained. This corresponds to a 4,6-dichloropyrimidine yield of 89.8% of theory.

Example 2

80 parts by weight of phosphorus oxychloride and 20 parts by weight of 4-chloro-6-methoxypyrimidine were introduced into a stirred vessel. The mixture was heated to 80° C. with stirring. Then gaseous hydrogen chloride was passed in at a rate of 12 parts by weight per hour. The passing in was stopped after 20 hours, and the mixture was cooled to room temperature and weighed. 93.5 parts by weight of reaction mixture were obtained. HPLC analysis showed 0.46% by weight of 4-chloro-6-methoxypyrimidine and 20.7% by weight of 4,6-dichloropyrimidine. This corresponds to a 4,6-dichloropyrimidine yield of 93.8% of theory.

Example 3

80 parts by weight of phosphorus oxychloride, 20 parts by weight of 4-chloro-6-methoxypyrimidine and 2 parts by weight of N,N-dimethylformamide were stirred at 80° C. Over the course of 6 hours, 25 parts by weight of gaseous hydrogen chloride were passed into this mixture at a constant rate. After cooling to room temperature, a reaction mixture in an amount of 87.2 parts by weight was obtained. HPLC analysis showed 0.17% by weight of 4-chloro-6-methoxypyrimidine and 23.3% by weight of 4,6-dichloropyrimidine. corresponding to a 4,6-dichloropyrimidine yield of 98.4% of theory.

The reaction mixture was subsequently extracted 6 times with 80 parts by weight of methylcyclohexane each time at 55° C. The combined extracts were evaporated in a rotary evaporator to result in 23.0 parts by weight of colorless crystalline needles which consisted of 4,6-dichloropyrimidine with an HPLC content of 96.9%.

Example 4

100 parts by weight of o-dichlorobenzene, 10 parts by weight of 4-chloro-6-methoxypyrimidine and 30 parts by weight of triphenyldichlorophosphorane were introduced into a stirred vessel and heated to 100° C. with stirring. Then 20 parts by weight of gaseous hydrogen chloride were blown in at a constant rate over the course of 4 hours. The mixture was then cooled to room temperature. This resulted in 141.0 parts by weight of reaction mixture. HPLC analysis thereof showed contents of 0.04% of 4-chloro-6-methoxypyrimidine and 7.02% of 4,6-dichloropyrimidine. This corresponds to a 4,6-dichloropyrimidine yield of 96% of theory.

Example 5

100 parts by weight of o-dichlorobenzene, 2 parts by weight of triphenyiphosphine oxide and 10 parts by weight of 4-chloro-6-methoxypyrimidine were introduced into a stirred vessel. The mixture was then heated to 130° C., and 10 parts by weight of gaseous hydrogen chloride were blown in together with 18 parts by weight of phosgene simultaneously at a constant rate over the course of 4 hours. The mixture was then cooled to room temperature. This resulted in 108.5 parts by weight of reaction mixture. HPLC analysis thereof showed contents of 0.08% 4-chloro-6-methoxypyrimidine and 9.37% 4,6-dichloropyrimidine. This corresponds to a 4,6-dichloropyrimidine yield of 98.6% of theory.

Example 6

110 parts by weight of chlorobenzene, 46 parts by weight of phosphorus pentachloride and 28.9 parts by weight of 4-chloro-6-methoxypyrimidine were introduced into a stirred vessel. The mixture was stirred at 100° C. and 20 parts by weight of gaseous hydrogen chloride were passed in at a constant rate in 8 hours. Cooling to room temperature resulted in 175 parts by weight of reaction mixture. HPLC analysis thereof showed 0.15% 4-chloro-6-methoxypyrimidine and 16.55% 4,6-dichloropyrimidine. This corresponds to a 4,6-dichloropyrimidine yield of 97.2% of theory.

Example 7

100 parts by weight of thionyl chloride, 30 parts by weight of phosphine oxide and 28.9 parts by weight of 4-chloro-6-methoxypyrimidine were introduced into a stirred vessel. The mixture was then heated to 80° C. with stirring. At this temperature, 25 parts by weight of gaseous hydrogen chloride were passed in at a constant rate over the course of 4 hours. Cooling to room temperature resulted in 130 parts by weight of a reaction mixture. HPLC analysis thereof showed 0.30% 4-chloro-6-methoxypyrimidine and 22.61% 4,6-dichloropyrimidine, which corresponds to a 4,6-dichloropyrimidine yield of 98.6% of theory.

Example 8

80 parts by weight of phosphorus oxychloride and 20 parts by weight of 4-chloro-6-methoxypyrimidine were introduced into a stirred vessel. The mixture was heated to 80° C. with stirring and, while stirring, 8 parts by weight of gaseous hydrogen chloride were passed in at a constant rate over the course of 5 hours. Then 7.5 parts by weight of phosphorus trichloride were added and 3.3 parts by weight of chlorine were blown in at 80° C. over the course of 30 minutes. A further 8 parts by weight of gaseous hydrogen chloride were then passed in over the course of 3 hours and, thereafter, a further 7.5 parts by weight of phosphorus trichloride were added, and 3.3 parts by weight of chlorine were added at 80° C. over the course of 30 minutes. Then, for the third time, 8 parts by weight of hydrogen chloride were passed in over the course of 3 hours, after which a further 7.5 parts by weight of phosphorus trichloride were added and again 3.3 parts by weight of chlorine were added at 80° C. over the course of 30 minutes. Subsequently phosphorus oxychloride and residues of phosphorus trichloride were distilled out of the reaction mixture under atmospheric pressure. This resulted in 99.2 parts by weight of a colorless distillate. The remaining residue of 24.0 parts by weight was distilled in vacuo (at 50 mbar). 18.6 parts by weight of a colorless distillate consisting of 4,6-dichloropyrimidine were obtained. This corresponds to a yield of 90.2% of theory. The HPLC content was 99.8%. 4-Chloro6-methoxypyrimidine was no longer present. The distillation residue comprised 5.1 parts by weight. It contained further 4,6-dichloropyrimidine corresponding to a yield of 2.9% of theory.

Example 9

100 parts by weight of chlorobenzene, 28 parts by weight of 4-chloro-6-methoxypyrimidine and 10 parts by weight of dimethylformamide were introduced into a stirred vessel. The mixture was heated to 100° C. with stirring and then 50 parts by weight of phosgene and 25 parts by weight of hydrogen chloride were passed in simultaneously and both at a constant rate over the course of 10 hours. The mixture was then cooled to room temperature. This resulted in 135.6 parts by weight of reaction mixture. BPLC analysis thereof showed a 4,6-dichloropyrimidine content of 18.7%, which corresponds to a yield of 85.1% of theory.

What is claimed is:

1. A process for preparing 4,6-dichloropyrimidine comprising reacting 4-chloro-6-methoxypyrimidine with an acid chloride in the presence of a hydrogen halide.

2. The process according to claim 1 wherein the acid chloride is $PCl_3$, $POCl_3$, $PCl_5$, R—$PCl_2$, R—$PCl_4$, R—$POCl_2$, or $R_3PCl_2$, where R represents $C_6$–$C_{10}$-aryl, substituted $C_6$–$C_{10}$-aryl, $C_1$–$C_{10}$-alkyl, or substituted $C_1$–$C_{10}$-alkyl; an acid chloride of the formula R'—CO—Cl, where R' represents chlorine, $C_1$–$C_{10}$-alkoxy, $C_6$–$C_{10}$-aryloxy, —O—$CCl_3$, —CO—Cl, or $C_5$–$C_{11}$-heteroaryloxy having 1 to 3 heteroatoms selected from the group consisting of N, O, and S, where the alkoxy, aryloxy, and heteroaryloxy radicals are optionally substituted; and $SOCl_2$.

3. The process according to claim 1 wherein the hydrogen halide is hydrogen chloride.

4. The process according to claim 3 wherein the hydrogen chloride is generated in situ from excess acid chloride and a protic compound.

5. The process according to claim 1 wherein at least 1 mol of acid chloride and at least 1 mol of hydrogen halide are used per mole of 4-chloro-6-methoxypyrimidine.

6. The process according to claim 1 carried out at a temperature in the range 0 to 200° C. and under a pressure in the range 0.1 to 50 bar.

* * * * *